United States Patent [19]
Klein et al.

[11] Patent Number: 5,140,018
[45] Date of Patent: Aug. 18, 1992

[54] 1,3,2-BENZODITHIAZOLE-1-OXIDE COMPOUNDS

[75] Inventors: Larry L. Klein, Lake Forest; Clinton M. Yeung, Skokie, both of Ill.

[73] Assignee: Abbott Laboratories, Abbott Park, Ill.

[21] Appl. No.: 696,662

[22] Filed: May 7, 1991

[51] Int. Cl.$^5$ .................. C07D 285/01; A61K 31/41
[52] U.S. Cl. ........................ 514/63; 514/360; 548/110; 548/123
[58] Field of Search ............... 548/123, 110; 514/360, 514/63

[56] References Cited

U.S. PATENT DOCUMENTS 3,490,893  1/1970  Ahle et al. ................... 548/123
4,911,754  3/1990  Hunt et al.
4,988,809  1/1991  Seidel et al. ................. 548/123

FOREIGN PATENT DOCUMENTS

3635696A1  4/1988  Fed. Rep. of Germany.

OTHER PUBLICATIONS

Massimo et al., Il Farmaco, 45(4):439–446 (1990).
Chen et al., Synthesis of 5-Methyl-1,3,2-benzodithiazoles, J. Heterocyclic Chem., 16:183 (1979).

Primary Examiner—Joseph Paul Brust
Assistant Examiner—M. S. H. Gabilen
Attorney, Agent, or Firm—Andreas M. Danckers

[57] ABSTRACT

Novel 1,3,2-benzodithiazole-1-oxides of formula (I)

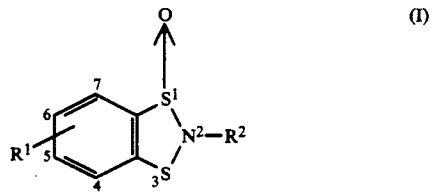

and their pharmaceutically acceptable salts are disclosed, wherein $R^1$ is a substituent on the 4-, 5-, 6- or 7-position of the benzodithiazole nucleus selected from the group consisting of hydrogen, ($C_1$–$C_4$)alkyl, halogen, halo($C_1$–$C_4$)alkyl, ($C_1$–$C_4$)alkoxy, and nitro; and $R^2$ is selected from the group consisting of ($C_1$–$C_{12}$)alkyl; substituted ($C_1$–$C_{12}$)alkyl; ($C_2$–$C_{16}$)alkenyl; ($C_2$–$C_{16}$)alkynyl; ($C_3$–$C_{10}$)cycloalkyl; ($C_6$–$C_{10}$)aryl; mono- or di-substituted ($C_6$–$C_{10}$)aryl; ($C_6$–$C_{10}$)aryl-($C_1$–$C_4$)alkyl; mono- or di-substituted ($C_6$–$C_{10}$)aryl-($C_1$–$C_4$)alkyl; heterocycle-($C_1$–$C_4$)alkyl; and mono- or di-substituted heterocycle-($C_1$–$C_4$)alkyl.

Also disclosed are the antifungal use and method of preparation of such compounds, as well as their formulation as pharmaceutical compositions.

9 Claims, No Drawings

1,3,2-BENZODITHIAZOLE-1-OXIDE COMPOUNDS

FIELD OF THE INVENTION

The present invention relates to novel benzodithiazole compounds and compositions containing these compounds, as well as the use thereof in treating fungal infections. The invention also relates to processes for preparing these compounds and synthetic intermediates employed therein.

BACKGROUND OF THE INVENTION

A variety of recent developments are responsible for an increase in the incidence and variety of fungal infections, including the intensive use of chemotherapy for bacterial infections, a wider use of catheterization, and an increase in the number of patients who are immune-suppressed due to organ transplantation and other medical procedures (cf., M. Rinaldi in *Infectious Disease Clinics of North America* Vol. 3, D. J. Drutz, Ed., B. Saunders Co., Philadelphia, 1989, p. 65). Many reports describe infections by fungi not previously recognized as human pathogens. In addition, the advent of AIDS has created a group of immuno-compromised patients who are predisposed to fungal infections with a unique pattern of infection. In this patient population, oral and esophageal Candida infections are prevalent and Cryptococcus has emerged as a major pathogen. As a result of these developments, the relative importance of the fungal pathogens has changed in recent years and there is an even greater need for effective antifungal agents.

Amphotericin B, a fungicidal agent of the polyene macrolide class, is effective against a number of fungal infections which prior to the availability of this drug were almost invariably fatal. However, amphotericin B is characterized by poor oral bioavailability and considerable mammalian toxicity, and is capable of causing a variety of untoward effects including anaphylaxis, thrombocytopenia, flushing, generalized pain, convulsions, chills, fever, phlebitis, headache, anemia, anorexia and decreased kidney function (M. W. DeGregorio, et. al., *Amer. J. Med.*, 1982, 73:543-548). Nephrotoxicity is an especially significant problem and 80% of patients treated with amphotericin B experience impaired kidney function. Much of the current work in antifungal research is directed to attempting to reduce the toxicity of amphotericin B by altering its pharmacokinetic properties, for example, cf., PCT Patent Application No. WO 90/1873, published Mar. 8, 1990, for aerosol formulations. Efforts to reduce the toxicity of amphotericin B by chemical modification have been unsuccessful thus far (P. D. Hoeprich, et al., *Ann. N.Y. Acad. Sci.*, 1988, 544:517). A recent survey also suggests that resistance to amphotericin B among species of Candida and Torulopsis is becoming a significant problem (W. G. Powderly, *Amer. J. Med.*, 1988, 84:826-832).

Ketoconazole, the leading member of the azole class of antifungal compounds, is orally active and has been used clinically for many years. Ketoconozole and other azoles also suffer from several disadvantages. For example, they are fungistatic and not fungicidal, are inhibitors of the biosynthesis of testosterone, are hepatotoxins and are poorly absorbed into the cerebrospinal fluid. Resistance to azole antifungal agents has also been documented.

In view of the scarcity of agents currently available to the physician, there is an evident need for accelerated development of new, more effective and less toxic antifungal drugs, especially for treating systemic fungal infections.

The compounds of the present invention comprise novel benzodithiazole-1-oxides. 1,2,3-Benzodithiazole-2-oxide and 1,3,2-benzodithiazole-1,1-dioxides have been previously described; they are not, however, known as antifungal agents. For example, J. L. Ahle and W. C. Doyle, in U.S. Pat. No. 3,490,893, issued Jan. 20, 1970, disclose 3H-1,2,3-benzodithiazole-2-oxides which are useful for combating weeds in small grains. J. Uhlendorf et al., in German Offenlegungsschrift Number DE 3635696, published Apr. 28, 1988, disclose benzo-1,3-2-dithiazol-1,1-dioxides said to be useful as antiflammatory and antiallergy agents.

The synthesis of 5-methyl-1,3,2-benzodithiazoles, intermediates in the preparation of the novel 1,3,2-benzodithiazole-1-oxides of the present invention, has been reported in the literature ((C. H. Chen and B. A. Donatelli, *J. Heterocyclic Chem.*, 1979, 16:183-185). These compounds were prepared as components of charge transfer salts, and are not known to have any biological activity.

G. Massimo, et al, *Il Farmaco*, 1990, 45:439-446 describe biological studies on 1,2-benzisothiazole-3-ones and report antibacterial and antifungal activity for these compounds. None of the above references, however, disclose or suggest the novel compounds of the present invention.

SUMMARY OF THE INVENTION

In one aspect of the present invention are provided benzodithiazole compounds of formula (I)

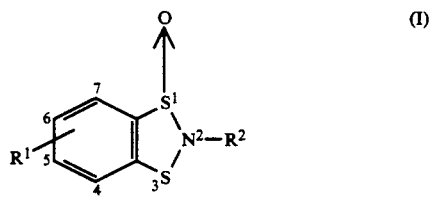

and pharmaceutically acceptable salts thereof, wherein $R^1$ is a substituent on the 4-, 5-, 6- or 7-position of the benzodithiazole nucleus selected from the group consisting of
 (1) hydrogen,
 (2) ($C_1$–$C_4$)alkyl,
 (3) halogen,
 (4) halo-($C_1$–$C_4$)alkyl,
 (5) ($C_1$–$C_4$)alkoxy, and
 (6) nitro; and
$R^2$ is selected from the group consisting of
 (1) ($C_1$–$C_{12}$)alkyl;
 (2) ($C_1$–$C_{12}$)alkyl substituted with a substituent selected from the group consisting of
  (i) hydroxy,
  (ii) —OS(O)$^2R^3$ wherein $R^3$ is ($C_1$–$C_4$)alkyl,
  (iii) —OSiR$^4$R$^5$R$^6$ wherein $R^4$, $R^5$ and $R^6$ are independently selected from methyl, ethyl, t-butyl and phenyl,
  (iv) —CHO or —C(OR$^7$)$_2$ wherein $R^7$ is methyl or ethyl,
  (v) —OC(O)R$^8$ wherein $R^8$ is ($C_1$–$C_4$)alkyl, and
  (vi) —C(O)OR$^{10}$ wherein $R^{10}$ is ($C_1$–$C_4$)alkyl;
 (3) ($C_2$–$C_{16}$)alkenyl;

(4) $(C_2-C_{16})$alkynyl;
(5) $(C_3-C_{10})$cycloalkyl;
(6) $(C_6-C_{10})$aryl;
(7) $(C_6-C_{10})$aryl substituted with 1 or 2 substituents selected from the group consisting of
(i) halogen,
(ii) halo-$(C_1-C_4)$alkyl,
(iii) methylenedioxy,
(iv) $(C_1-C_4)$alkoxy,
(v) —CHO or —$C(OR^7)_2$ wherein $R^7$ is methyl or ethyl,
(vi) —$C(O)OR^{10}$ wherein $R^{10}$ is $(C_1-C_4)$alkyl, and
(vii) —$NR^{11}R^{12}$ wherein $R^{11}$ and $R^{12}$ are $(C_1-C_4)$alkyl;
(8) $(C_6-C_{10})$aryl-$(C_1-C_4)$alkyl;
(9) $(C_6-C_{10})$aryl-$(C_1-C_4)$alkyl wherein the aryl group is substituted with 1 or 2 substituents selected from the group consisting of
(i) halogen,
(ii) $(C_1-C_4)$alkyl,
(iii) halo-$(C_1-C_4)$alkyl,
(iv) $(C_1-C_4)$alkoxy,
(v) methylenedioxy, and
(vi) —$NR^{11}R^{12}$ wherein $R^{11}$ and $R^{12}$ are $(C_1-C_4)$alkyl;
(10) heterocycle-$(C_1-C_4)$alkyl; and
(11) heterocycle-$(C_1-C_4)$alkyl wherein the heterocyclic group is substituted with 1 or 2 substituents selected from the group consisting of
(i) halogen,
(ii) $(C_1-C_4)$alkyl,
(iii) halo-$(C_1-C_4)$alkyl,
(iv) $(C_1-C_4)$alkoxy,
(v) methylenedioxy, and
(vi) —$NR^{11}R^{12}$ wherein $R^{11}$ and $R^{12}$ are $(C_1-C_4)$alkyl.

In another aspect of the present invention are provided pharmaceutical compositions for treating fungal infections, comprising a therapeutically effective amount of a compound of the invention and a pharmaceutically acceptable carrier.

In a further aspect of the present invention is provided a method of treating fungal infections, comprising administering to a human or lower mammal in need of such treatment a therapeutically effective amount of a compound of formula (I).

In yet another aspect of the present invention is provided a process for the preparation of the compounds of the invention, comprising the step of oxidizing a benzodithiazole with a suitable oxidizing agent.

DETAILED DESCRIPTION OF THE INVENTION

The present invention comprises novel 1,3,2-benzodithiazole-1-oxides useful as antifungal agents, of which the following compounds are representative:

2-(2-phenylethyl)-1,3,2-benzodithiazole-1-oxide;
2-methyl-1,3,2-benzodithiazole-1-oxide;
2-n-propyl-1,3,2-benzodithiazole-1-oxide;
2-n-pentyl-1,3,2-benzodithiazole-1-oxide;
2-n-heptyl-1,3,2-benzodithiazole-1-oxide;
2-n-octyl-1,3,2-benzodithiazole-1-oxide;
2-n-nonyl-1,3,2-benzodithiazole-1-oxide;
2-n-decyl-1,3,2-benzodithiazole-1-oxide;
2-n-hexadecyl-1,3,2-benzodithiazole-1-oxide;
2-allyl-1,3,2-benzodithiazole-1-oxide;
2-oleyl-1,3,2-benzodithiazole-1-oxide;
2-propargyl-1,3,2-benzodithiazole-1-oxide;
2-(3-pentyl)-1,3,2-benzodithiazole-1-oxide;
2-t-butyl-1,3,2-benzodithiazole-1-oxide;
2-(3,3-dimethylpropyl)-1,3,2-benzodithiazole-1-oxide;
2-(1,1,3,3-tetramethylbutyl)-1,3,2-benzodithiazole-1-oxide;
2-(2-methoxy-1-methylethyl)-n-nonyl-1,3,2-benzodithiazole-1-oxide;
2-(2-hydroxyethyl)-1,3,2-benzodithiazole-1-oxide;
O-(2-(1,3,2-benzodithiazole-2-yl-1-oxide)ethyl)methanesulfonate;
2-(2-(triethylsilyloxy)ethyl)-1,3,2-benzodithiazole-1-oxide;
ethyl 2-(1,3,2-benzodithiazole-2-yl-1-oxide)-acetate;
2-(2-(1,3,2-benzodithiazole-2-yl-1-oxide)ethyloxy) acetic acid;
2-(3-(N,N-dimethylamino)-n-propyl)-1,3,2-benzodithiazole-1-oxide;
2-(2-(1-piperidinyl)ethyl)-1,3,2-benzodithiazole-1-oxide;
2-(4,4-diethoxybutyl)-1,3,2-benzodithiazole-1-oxide;
methyl 8-(1,3,2-benzodithiazole-2-yl)-octanoate;
2-cyclopropyl-1,3,2-benzodithiazole-1-oxide;
2-cyclooctyl-1,3,2-benzodithiazole-1-oxide;
2-(2-adamantyl)-1,3,2-benzodithiazole-1-oxide;
2-phenyl-1,3,2-benzodithiazole-1-oxide;
2-(1,2-benzodioxole-4-yl)-1,3,2-benzodithiazole-1-oxide;
2-(3,4-difluorophenyl)-1,3,2-benzodithiazole-1-oxide;
2-(2-furanyl)methyl-1,3,2-benzodithiazole-1-oxide;
2-(2-thienyl)methyl-1,3,2-benzodithiazole-1-oxide;
2-benzyl-1,3,2-benzodithiazole-1-oxide;
2-(2,4-dichlorophenyl)methyl-1,3,2-benzodithiazole-1-oxide;
2-(4-(dimethylamino)phenyl)methyl-1,3,2-benzodithiazole-1-oxide
2-(2-(4-pyridyl)ethyl)-1,3,2-benzodithiazole-1-oxide;
2-(3-phenylpropyl)-1,3,2-benzodithiazole-1-oxide;
2-n-octyl-5-methyl-1,3,2-benzodithiazole-1-oxide;
2-n-octyl-6-methyl-1,3,2-benzodithiazole-1-oxide;
2-phenylmethyl-5-methyl-1,3,2-benzodithiazole-1-oxide;
2-phenylmethyl-6-methyl-1,3,2-benzodithiazole-1-oxide;
5-chloro-2-n-octyl-1,3,2-benzodithiazole-1-oxide;
6-chloro-2-n-octyl-1,3,2-benzodithiazole-1-oxide;
5-fluoro-2-n-octyl-1,3,2-benzodithiazole-1-oxide;
6-fluoro-2-n-octyl-1,3,2-benzodithiazole-1oxide;
5-methoxy-2-n-octyl-1,3,2-benzodithiazole-1-oxide;
6-methoxy-2-n-octyl-1,3,2-benzodithiazole-1-oxide;
5-ethyl-2-n-octyl-1,3,2-benzodithiazole-1-oxide;
6-ethyl-2-n-octyl-1,3,2-benzodithiazole-1-oxide;
5-nitro-2-n-octyl-1,3,2-benzodithiazole-1-oxide;
6-nitro-2-n-octyl-1,3,2-benzodithiazole-1-oxide;
2-allyl-5-chloro-1,3,2-benzodithiazole-1-oxide;
2-allyl-6-chloro-1,3,2-benzodithiazole-1-oxide;
2-allyl-5-fluoro-1,3,2-benzodithiazole-1-oxide;
2-allyl-6-fluoro-1,3,2-benzodithiazole-1-oxide;
2-allyl-5-methoxy-1,3,2-benzodithiazole-1-oxide;
2-allyl-6-methoxy-1,3,2-benzodithiazole-1-oxide;
2-allyl-5-ethyl-1,3,2-benzodithiazole-1-oxide;
2-allyl-6-ethyl-1,3,2-benzodithiazole-1-oxide;
2-allyl-5-nitro-1,3,2-benzodithiazole-1-oxide;
2-allyl-6-nitro-1,3,2-benzodithiazole-1-oxide;
5-chloro-2-propargyl-1,3,2-benzodithiazole-1-oxide;
6-chloro-2-propargyl-1,3,2-benzodithiazole-1-oxide;
5-fluoro-2-propargyl-1,3,2-benzodithiazole-1-oxide;
6-fluoro-propargyl-1,3,2-benzodithiazole-1-oxide;
5-methoxy-propargyl-1,3,2-benzodithiazole-1-oxide;

6-methoxy-propargyl-1,3,2-benzodithiazole-1-oxide;
5-ethyl-2-propargyl-1,3,2-benzodithiazole-1-oxide;
6-ethyl-2-propargyl-1,3,2-benzodithiazole-1-oxide;
5-nitro-2-propargyl-1,3,2-benzodithiazole-1-oxide;
6-nitro-2-propargyl-1,3,2-benzodithiazole-1-oxide;
2-benzyl-5-chloro-1,3,2-benzodithiazole-1-oxide;
2-benzyl-6-chloro-1,3,2-benzodithiazole-1-oxide;
2-benzyl-5-fluoro-1,3,2-benzodithiazole-1-oxide;
2-benzyl-6-fluoro-1,3,2-benzodithiazole-1-oxide;
2-benzyl-5-methoxy-1,3,2-benzodithiazole-1-oxide;
2-benzyl-6-methoxy-1,3,2-benzodithiazole-1-oxide;
2-benzyl-5-ethyl-1,3,2-benzodithiazole-1-oxide;
2-benzyl-6-ethyl-1,3,2-benzodithiazole-1-oxide;
2-benzyl-5-nitro-1,3,2-benzodithiazole-1-oxide; and
2-benzyl-6-nitro-1,3,2-benzodithiazole-1-oxide;
as well as pharmaceutically acceptable salts thereof.

Compounds which are representative of the preferred compounds of the invention are those in which $R^2$ is selected from $(C_1-C_9)$alkyl, $(C_3-C_9)$alkenyl, $(C_3-C_9)$alkynyl and phenyl-$(C_1-C_4)$alkyl. Such compounds include the following:

2-(2-phenylethyl)-1,3,2-benzodithiazole-1-oxide;
2-methyl-1,3,2-benzodithiazole-1-oxide;
2-n-propyl-1,3,2-benzodithiazole-1-oxide;
2-n-heptyl-1,3,2-benzodithiazole-1-oxide;
2-n-octyl-1,3,2-benzodithiazole-1-oxide;
2-n-nonyl-1,3,2-benzodithiazole-1-oxide;
2-allyl-1,3,2-benzodithiazole-1-oxide;
2-propargyl-1,3,2-benzodithiazole-1-oxide;
2-t-butyl-1,3,2-benzodithiazole-1-oxide;
2-cyclopropyl-1,3,2-benzodithiazole-1-oxide;
2-benzyl-1,3,2-benzodithiazole-1-oxide;
2-n-octyl-5-methyl-1,3,2-benzodithiazole-1-oxide;
2-n-octyl-6-methyl-1,3,2-benzodithiazole-1-oxide;
2-phenylmethyl-5-methyl-1,3,2-benzodithiazole-1-oxide; and
2-phenylmethyl-6-methyl-1,3,2-benzodithiazole-1-oxide;
as well as pharmaceutically acceptable salts thereof.

Compounds which are representative of the particularly preferred compounds of the present invention include:

2-n-heptyl-1,3,2-benzodithiazole-1-oxide;
2-n-octyl-1,3,2-benzodithiazole-1-oxide;
2-allyl-1,3,2-benzodithiazole-1-oxide;
2-propargyl-1,3,2-benzodithiazole-1-oxide; and
2-benzyl-1,3,2-benzodithiazole-1-oxide;
as well as the pharmaceutically acceptable salts thereof.

The following terms are used as defined below throughout this disclosure and in the appended claims.

The term "$(C_2-C_{16})$alkenyl" as used herein refers to a straight or branched chain of from two to sixteen carbon atoms which contains a carbon-carbon double bond including, but not limited to, vinyl, allyl, methallyl, propenyl, butenyl, isoprenyl, oleyl and the like.

The term "$(C_1-C_4)$alkoxy" as used herein refers to —$OR^{13}$ wherein $R^{13}$ is $(C_1-C_4)$alkyl.

The term "alkyl" as used herein, in connection with "$(C_1-C_{12})$alkyl", refers to straight or branched chain alkyl radicals having either from one to twelve carbon atoms including, but not limited to, methyl, ethyl, propyl, isopropyl, butyl, isobutyl, sec-butyl, pentyl, hexyl, heptyl, 1,1,3,3-tetramethylbutyl, n-decyl, dodecyl and the like; or, in connection with "$(C_1-C_4)$alkyl", refers to one to four carbon atoms as for example methyl, ethyl, propyl, isopropyl, butyl, isobutyl, sec-butyl, t-butyl and the like.

The term "$(C_2-C_{16})$alkynyl" as used herein refers to a straight or branched chain of from two to sixteen carbon atoms which contains a carbon-carbon triple bond including, but not limited to, ethynyl, propynyl, 2-pentynyl, 3-pentynyl, 4-pentynyl, propargyl and the like.

The term "$(C_6-C_{10})$aryl" refers to a monocyclic or bicyclic aromatic radical, such as a phenyl, naphthyl, indanyl, dihydronaphthyl or tetrahydronaphthyl radical, which may be substituted with one or two substituents independently selected from the following groups: halogen, halo$(C_1-C_4)$alkyl, $(C_1-C_4)$alkoxy, methylenedioxy, $(C_1-C_4)$alkyl and —$NR^{11}R^{12}$, wherein $R^{11}$ and $R^{12}$ are $(C_1-C_4)$alkyl.

The term "$(C_6-C_{10})$aryl-$(C_1-C_4)$alkyl" or "aralkyl" refers to a $(C_1-C_4)$alkyl group substituted with an aryl group, as defined above. Examples of aralkyl groups include benzyl, phenylethyl, dichlorophenylmethyl, phenylpropyl, naphthylmethyl and the like. The aryl group may, further, be substituted with one or two substituents independently selected from the following groups: halogen, halo$(C_1-C_4)$alkyl, $(C_1-C_4)$alkoxy, methylenedioxy, $(C_1-C_4)$ alkyl and —$NR^{11}R^{12}$, wherein $R^{11}$ and $R^{12}$ are $(C_1-C_4)$alkyl.

The term "$(C_3-C_{10})$cycloalkyl" as used herein refers to monocyclic, bicyclic and tricyclic alkyl radical having from three to ten carbon atoms which may contain 0, 1 or 2 carbon-carbon double bonds including, but not limited to, cyclopropyl, cyclobutyl, cyclopentyl, cyclopentenyl, cyclohexyl, cycloheptyl, cyclooctyl, norbornyl, norbornenyl, adamantyl, camphenyl, pinenyl and the like.

The term "halo" or "halogen" as used herein refers to chloro, bromo, iodo or fluoro.

The term "halo$(C_1-C_4)$alkyl" as used herein refers to a $(C_1-C_4)$alkyl radical, as defined above, in which one or more hydrogen atoms are replaced with halogen including, but not limited to, chloromethyl, fluoromethyl, dichloroethyl, trifluoromethyl, bromoethyl, fluoropropyl and the like.

The term "heterocycle-$(C_1-C_4)$alkyl" as used herein refers to a 5- or 6-membered ring containing one, two or three nitrogen atoms; one sulfur atom; one nitrogen and one sulfur atom; one oxygen atom; or one nitrogen and one oxygen atom; wherein the 5-membered ring has 0-2 double bonds and the 6-membered ring has 0-3 double bonds; wherein the nitrogen and sulfur heteroatoms may optionally be oxidized; and wherein the nitrogen heteroatoms may optionally be quaternized. Heterocycles include, but are not limited to, pyridyl, thienyl, pyrimidinyl, tetrahydrofuryl, imidazolyl, oxazolyl, isoxazolyl, piperazinyl, piperidinyl, pyrrolyl, pyrrolidinyl, pyrazolyl, thiazolyl, morpholino, thiomorpholino and the like. Heterocycles may be optionally substituted with one or two substituents independently selected from $(C_1-C_4)$alkyl, halogen, halo$(C_1-C_4)$alkyl, $(C_1-C_4)$alkoxy and —$NR^{11}R^{12}$ wherein $R^{11}$ and $R^{12}$ are independently selected from $(C_1-C_4)$alkyl and —$C(O)R^{14}$ wherein $R^{14}$ is $(C_1-C_4)$alkyl.

As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator.

By a "therapeutically effective amount" of a compound of the invention is meant a sufficient amount of the compound to treat a fungal infection, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, of from about 0.01 to about 25 mg/kg body weight or, more usually, from about 0.1 to about 15 mg/kg body weight. Single dose compositions may contain such amounts or submultiples thereof as make up the daily dose. In general, treatment regimens according to the present invention comprise administration to a patient in need of such treatment of from about 10 mg to about 1000 mg of the compound(s) of this invention per day in multiple doses or in a single dose.

Liquid dosage forms for oral administration may include pharmaceutically acceptable emulsions, microemulsions, solutions, suspensions, syrups and elixirs containing inert diluents commonly used in the art such as water. Such composition may also comprise adjuvants such as wetting agents; emulsifying or suspending agents and sweetening, flavoring or perfuming agents.

Injectable preparations, as for example sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, as for example in solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid may be used in the preparation of injectables.

The injectable formulation can be sterilized, as for example by filtration through a bacteria-retaining filter or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, as for example, its crystal size and crystalline form. Another approach to delaying absorption of a drug is to administer the drug as a solution or suspension in oil. Injectable depot forms can also be made by forming microcapsule matrices of drugs and biodegradable polymers such as polyactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter or polyethylene glycol which are solid at room temperature but liquid at the body-temperature and will therefore melt in the rectum and release the drug.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such exipients as lactose or milk sugar as well as high molecular weight polyethylene glycols and the like.

The active compounds can also be combined in micro-encapsulated form with one or more excipients as noted above. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solution are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates or polyamide powder, or mixtures of these substances. Sprays can additionally contain customary propellants such as chlorofluorohydrocarbons or substitutes therefor.

Transdermal patches have the added advantage of providing controlled delivery of a compound to the body. Such dosage forms can be made by dissolving or dispersing the compound in a suitable medium. Absorption enhancers can also be used to increase the flux of the compound across the skin. The rate can be controlled either by providing a rate controlling membrane or by dispersing the compound in a polymer matrix or gel.

The compounds of the present invention may be synthesized according to reaction Schemes I and II presented below, in which $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ correspond to the groups defined with respect to formula (I), as well as by using the reactions and techniques described in this section. The reactions are performed in a solvent appropriate to the reagents and materials employed and suitable for the transformation being effected. It will be understood by those skilled in the art of organic synthesis that the functionality present on the heterocycle and other portions of the molecule must be consistent with the chemical transformation proposed. This will frequently necessitate judgment as to the order of synthetic steps, protecting groups required and deprotection conditions. Throughout the following section, not all compounds of formula (I) falling into a given class may necessarily be prepared by all methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used.

SCHEME I

According to reaction Scheme I shown below, compounds of Formula 1 are treated with chlorine gas in an inert solvent, for example a chlorinated hydrocarbon such as carbon tetrachloride, methylene chloride or 1,2-dichloroethane, preferably at a reaction temperature of less than 20° C., more preferably at 0° C., to afford a compound of Formula 2, as described by Chen and Donatelli in *J. Heterocyclic Chem.*, 1979, 16:183-5. The compounds of Formula 2, in turn, are condensed as described by Chen and Donatelli (ibid), with an amine of Formula 3 to afford the benzodithiazole compounds of Formula 4. The condensation reaction may be conducted at a temperature of from about −50° C. to about 50° C. (preferably at a temperature less than 0° C. and more preferably at a temperature of from about −15° C. to −30° C.) in a suitable organic solvent such as diethyl ether, tetrahydrofuran, pyridine, methylene chloride, chloroform or 1-methyl-2-pyrrolidinone. It is desirable to carry out the reaction in the presence of an acid-acceptor such as triethylamine, N,N-dimethylaminopyridine (DMAP), potassium carbonate and the like, at a molar ratio of from 1.0 to 2.5 moles of the acid acceptor per mole of compound of the formula 2. The amine may also be used as an acid acceptor in which case two or more equivalents of this reagent is used. The compounds of Formula 4 are then oxidized by treatment with a suitable mild oxidizing agent as for example an organic peroxide such as 3-chloroperoxybenzoic acid (mCPBA) or monoperoxyphthalic acid magnesium salt hexahydrate (MMPP) or with an organic oxidizing agent such as pyridinium chlorochromate (PCC), pyridine-sulfur trioxide, pyridinium dichromate (PDC) or t-butyl hypochlorite, or alternately, with a mild inorganic oxidizing agent such as hydrogen peroxide, sodium iodate, sodium perborate, manganese dioxide and the like, to afford the compounds of formula (I).

SCHEME I

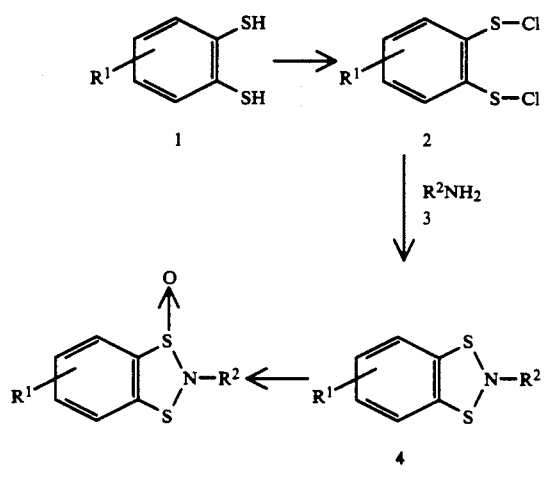

Accordingly, representative of the process of the present invention is the preparation of a compound of formula (I) by oxidizing a benzodithiazole having the formula

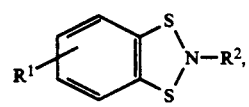

wherein $R^1$ and $R^2$ are as previously defined. Also representative of the process of the invention is the preparation of a compound of formula (I) from a benzodithiazole using a suitable oxidizing agent, such as one selected from those just described.

SCHEME II

Dithiols of formula 1 which are not commerically available are readily prepared according to reaction Scheme II. An aromatic thiol of formula 5 is treated with bis-(2,4-dicarboethoxymethylene)-1,3-dithietane to afford a thioester compound of formula 7. The thioesters of formula 7 are, in turn, treated with a mineral acid, such as sulfuric acid to produce the 2-ylidene-1,3-benzodithiole compounds of formula 8. The compounds of formula 8 may be treated with ethylenediamine to afford the dithiols of formula 1. Preferably, however, the compounds of formula 8 are treated with ethylenediamine in the presence of zinc acetate in order to isolate the insoluble zinc salt of the dithiol. The dithiol may then be released from its zinc salt by treatment with either acid or base according to known procedures (R.E.D. Clark, *Analyst*, 1957, 82:182) to afford the compounds of formula 1. The compounds of formula 1 are valuable intermediates and are converted to the compounds of formula (I) as shown above in reaction Scheme I.

SCHEME II

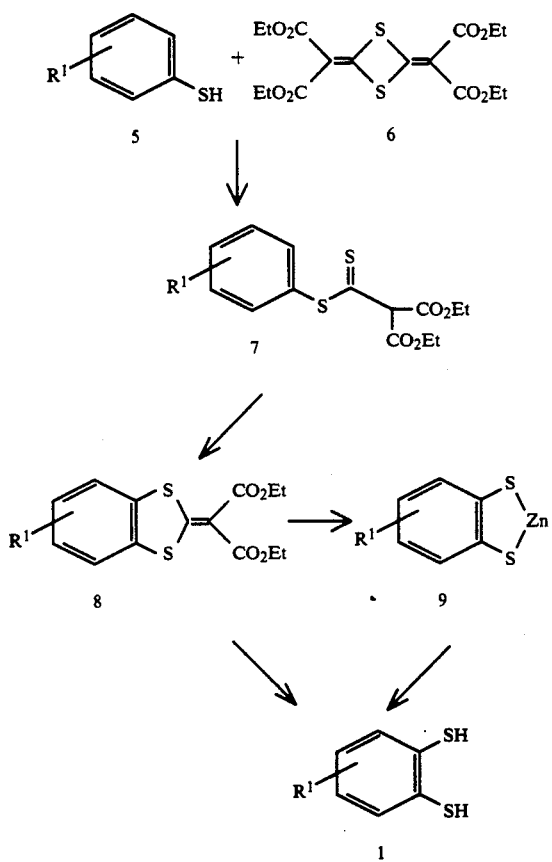

The foregoing may be better understood by reference to the following examples, which are provided for illustration only and are not intended as a limitation of the invention.

EXAMPLE 1

2-(2-Phenylethyl)-1,3,2-benzodithiazole-1-oxide

Step 1: 1,2-Benzodisulfenyl chloride

Chlorine gas (9.6 mL, 3 equivalents) was bubbled through a cooled (0° C.) solution of 1,2-benzenedithiol (10 g, 70 mmol) in 200 mL of carbon tetrachloride ($CCl_4$) over a period of an hour. The reaction mixture was stirred for an additional hour at 0° C. and then concentrated in vacuo at ambient temperature to give 13.4 g (90% yield) of the title compound as an orange solid.

Step 2: 2-(2-Phenylethyl)-1,3,2-benzodithiazole

A solution of 1,2-benzodisulfenyl chloride (0.9 g, 4.26 mmol), from Step 1, in 10 mL of diethyl ether was added dropwise over a period of 20 minutes to a mixture of phenylethylamine (0.54 mL, 4.30 mmol), triethylamine (1.2 mL, 9.0 mL, 10.5 mmol) and 100 mL of diethyl ether at −20° C. The reaction mixture was kept at −20° C. for one hour and then at ambient temperature for 16 hours. After filtration to remove the triethylamine hydrochloride, the filtrate was concentrated in vacuo. The residue was purified by column chromatography on silica gel eluting with hexane to give 62.6 mg (56.7% yield) of the title compound.

Step 3: 2-(2-Phenylethyl)-1,3,2-benzodithiazole-1-oxide

To a solution of 2-(2-phenylethyl)-1,3,2-benzodithiazole (0.538 g, 2.08 mmol), from Step 2, in 30 mL of chloroform at −20° C., was added portionwise 56% meta-chloroperoxybenzoic acid (mCPBA) (0.64 g, 2 mmol). The reaction mixture was allowed to warm to 0° C. over a 2 hour period and then the reaction was quenched at 10° C. with 20 mL of 1M aqueous sodium bicarbonate solution. The organic layer was concentrated in vacuo and the residue was purified by column chromatography on silica gel eluting with chloroform ($CHCl3$) to give 389 mg (65.7% yield) of the title compound. Analysis calculated for $C_{14}H_{13}NOS_2$: C, 61.08; H, 4.76; N, 5.09. Found: C, 60.92; H, 4.75; N, 5.04.

EXAMPLES 2–41

By following the procedures described in Example 1 and replacing phenylethylamine in Step 2 with the appropriate amine, Examples 2–41 were prepared as disclosed in Table 1. In the case of Examples 40 and 41, 1,2-benzenedithiol was also replaced with 4-methyl-1,2-benzenedithiol in Step 1. The structure of each product was confirmed by spectral analysis, and by elemental analysis or high resolution mass spectral (HRMS) analysis. The results of the elemental analyses or the HRMS analyses are shown in Table 1 for each compound. Most of the required amine starting materials are commercially available. Those which are not commercially available are readily prepared from commercially available compounds by methods well known to those skilled in the art.

TABLE 1

| EXAMPLE NO. | $R^1$ | $R^2$ | ELEMENTAL ANALYSIS | | |
|---|---|---|---|---|---|
| | | | C | H | N |

Examples 2–8

TABLE 1-continued

| EXAMPLE NO. | R¹ | R² | ELEMENTAL ANALYSIS | | |
|---|---|---|---|---|---|
| | | | C | H | N |

Examples 2-8: benzodithiazole with S=O, R¹ on ring, N–R²

| 2 | H | —CH₃ | CALCD: 45.41 | 3.81 | 7.57 |
| | | | FOUND: 45.61 | 3.82 | 7.54 |
| 3 | H | —CH₂CH₂CH₃ | CALCD: 50.7 | 5.20 | 6.57 |
| | | | FOUND: 50.3 | 4.88 | 6.77 |
| 4 | H | —CH₂(CH₂)₃CH₃ | CALCD: 241.0595 (*HRMS) | | |
| | | | FOUND: 241.0595 | | |
| 5 | H | —CH₂(CH₂)₅CH₃ | CALCD: 57.97 | 7.12 | 5.20 |
| | | | FOUND: 58.28 | 7.21 | 5.44 |
| 6 | H | —CH₂(CH₂)₆CH₃ | CALCD: 59.34 | 7.48 | |
| | | | FOUND: 59.05 | 7.29 | |
| 7 | H | —CH₂(CH₂)₇CH₃ | CALCD: 60.58 | 7.80 | 4.71 |
| | | | FOUND: 60.73 | 7.52 | 4.74 |
| 8 | H | —CH₂(CH₂)₈CH₃ | CALCD: 67.71 | 8.10 | 4.50 |
| | | | FOUND: 61.99 | 8.21 | 4.51 |

Examples 9-15

| 9 | H | —CH₂(CH₂)₁₄CH₃ | CALCD: 66.80 | 9.43 | 3.54 |
| | | | FOUND: 66.64 | 9.38 | 3.49 |
| 10 | H | —CH₂CH=CH₂ | CALCD: 51.18 | 4.3 | 6.64 |
| | | | FOUND: 50.94 | 4.26 | 6.59 |
| 11 | H | —(CH₂)₈CH=CH(CH₂)₈CH₃ | CALCD: 68.37 | 9.33 | 3.52 |
| | | | FOUND: 68.58 | 9.29 | 3.8 |
| 12 | H | —CH₂C≡CH | CALCD: 208.9969 (*HRMS) | | |
| | | | FOUND: 208.9972 | | |
| 13 | H | —CH(CH₂CH₃)₂ | CALCD: 54.76 | 6.27 | 5.81 |
| | | | FOUND: 55.13 | 6.34 | 5.75 |
| 14 | H | —C(CH₃)₃ | CALCD: 227.0439 (HRMS*) | | |
| | | | FOUND: 227.0438 | | |
| 15 | H | —(CH₂)₂C(CH₃)₃ | CALCD: 56.45 | 6.72 | 5.49 |
| | | | FOUND: 56.39 | 6.74 | 5.41 |

Examples 16-22

| 16 | H | —C(CH₃)₂CH₂C(CH₃)₃ | CALCD: 59.34 | 7.48 | 4.95 |
| | | | FOUND 59.31 | 7.52 | 4.92 |
| 17 | H | —CH(CH₃)CH₂OCH₃ | CALCD: 243.0388 (*HRMS) | | |
| | | | FOUND: 143.0389 | | |
| 18 | H | —CH₂CH₂OH | CALCD: 44.65 | 4.22 | 6.51 |
| | | | FOUND: 44.42 | 4.32 | 6.41 |
| 19 | H | —CH₂CH₂S(O)₂CH₃ | DCl/NH₃ MS M/Z: 311 (M+NH₄)⁺; ¹H NMR (CDCl₃) δ 3.0 (s, 3H), 3.8–4.0 (m, 2H), 4.4–4.6 (m, 2H), 7.3–7.4 (m, 1H), 7.5–7.6 (m, 2H), 7.85 (d, 1H). | | |
| 20 | H | —CH₂CH₂OSi(CH₂CH₃)₃ | CALCD: 51.05 | 7.04 | 4.26 |
| | | | FOUND: 50.65 | 7.01 | 4.22 |
| 21 | H | —(CH₂)₂C(O)CH₃ | CALCD: 257.0180 (HRMS*) | | |
| | | | FOUND: 257.0181 | | |
| 22 | H | —(CH₂)₂CH₂COOH | CALCD: 273.0130 (HRMS*) | | |
| | | | FOUND: 273.0129 | | |

Examples 23-30

TABLE 1-continued

| EXAMPLE NO. | R¹ | R² | ELEMENTAL ANALYSIS | | |
|---|---|---|---|---|---|
| | | | C | H | N |

Structure for Examples (above): benzo-fused ring with S—N(R²)—S, S=O, with R¹ substituent.

| EXAMPLE NO. | R¹ | R² | | C | H | N |
|---|---|---|---|---|---|---|
| 23 | H | —CH₂CH₂CH₃N(CH₃)₂ | CALCD: | 51.55 | 6.30 | 10.94 |
| | | | FOUND: | 51.28 | 6.38 | 10.74 |
| 24 | H | (propyl-piperidine) | CALCD: | 55.30 | 6.43 | 9.93 |
| | | | FOUND: | 55.25 | 6.37 | 9.64 |
| 25 | H | —(CH₂)₃CH(OEt)₂ | CALCD: | 53.32 | 6.72 | 4.44 |
| | | | FOUND: | 53.22 | 6.79 | 4.39 |
| 26 | H | —(CH₂)₇C(O)OCH₃ | CALCD: | 327.0963 (*HRMS) | | |
| | | | FOUND: | 327.0964 | | |
| 27 | H | cyclopropyl | CALCD: | 51.18 | 4.30 | 6.64 |
| | | | FOUND: | 51.12 | 4.22 | 6.60 |
| 28 | H | cyclooctyl | CALCD: | 59.77 | 6.81 | 4.98 |
| | | | FOUND: | 59.53 | 6.74 | 4.93 |
| 29 | H | adamantyl | CALCD: | 62.93 | 6.28 | 4.59 |
| | | | FOUND: | 62.70 | 6.22 | 4.52 |
| 30 | H | phenyl | CALCD: | 58.30 | 3.67 | 5.67 |
| | | | FOUND: | 57.91 | 3.56 | 5.64 |

Examples 31–38

Structure: benzo-fused ring with S—N(R²)—S, S=O, with R¹ substituent.

| EXAMPLE NO. | R¹ | R² | | C | H | N |
|---|---|---|---|---|---|---|
| 31 | H | 3,4-methylenedioxyphenyl | CALCD: | 53.61 | 3.12 | 4.81 |
| | | | FOUND: | 53.24 | 3.01 | 4.97 |
| 32 | H | 3,4-difluorophenyl | CALCD: | 50.88 | 2.49 | 4.95 |
| | | | FOUND: | 50.89 | 2.48 | 4.99 |
| 33 | H | furyl-ethyl | CALCD: | 52.59 | 3.61 | 5.58 |
| | | | FOUND: | 52.38 | 3.65 | 5.51 |

| EXAMPLE NO. | R¹ | R² | | ELEMENTAL ANALYSIS | | |
|---|---|---|---|---|---|---|
| | | | | C | H | N |
| 34 | H | 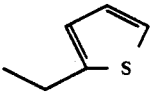 | CALCD: FOUND: | 49.44 49.15 | 3.40 3.44 | 5.36 5.21 |
| 35 | H | 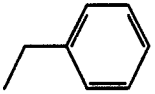 | CALCD: FOUND: | 59.76 59.69 | 4.25 4.31 | 5.36 5.34 |
| 36 | H | 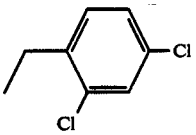 | CALCD: FOUND: | 47.28 47.17 | 2.75 2.77 | 4.24 4.41 |
| 37 | H | 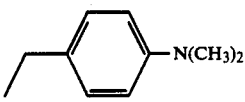 | CALCD: FOUND: | 304.0704 (*HRMS) 304.0703 | | |
| 38 | H | 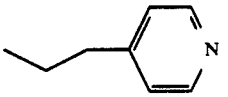 | CALCD: FOUND: | 56.51 56.56 | 4.38 4.48 | 10.15 10.02 |

Examples 39–41

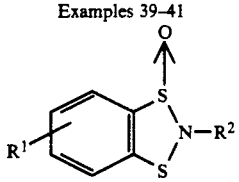

| 39 | H | 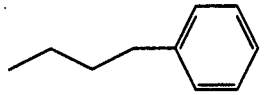 | CALCD: FOUND: | 62.27 62.15 | 5.23 5.33 | 4.84 4.77 |
| 40 | —CH₃ | —CH₂(CH₂)₆CH₃ | CALCD: FOUND: | 60.58 60.61 | 7.80 7.91 | 4.71 4.66 |
| 41 | —CH₃ | 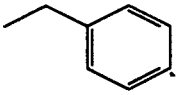 | CALCD: FOUND: | 61.08 60.74 | 4.76 4.78 | 5.09 5.06 |

(In the above Table, *HRMS = high resolution mass spectral data.)

EXAMPLES 42–81

Examples 42–81, shown below in Table 2, may be prepared by following the procedures shown in Scheme I and described in Example 1, replacing phenylethylamine in Step 2 with the appropriate amine, and replacing benzenedithiol in Step 1 with the appropriate substituted benzenedithiol, prepared as described by C. M. Yeung and L. L. Klein in *Tetrahedron Letters*, 1990, 31:2121–2124 and as shown herein in Scheme II.

TABLE 2

| Examples 42–81 | | | | | |
|---|---|---|---|---|---|
| Example # | R¹ | R² | Example # | R¹ | R² |
| 42 | 5-Cl | n-octyl | 62 | 5-Cl | propargyl |
| 43 | 6-Cl | n-octyl | 63 | 6-Cl | propargyl |
| 44 | 5-F | n-octyl | 64 | 5-F | propargyl |
| 45 | 6-F | n-octyl | 65 | 6-F | propargyl |
| 46 | 5-OMe | n-octyl | 66 | 5-OMe | propargyl |
| 47 | 6-OMe | n-octyl | 67 | 6-OMe | propargyl |
| 48 | 5-Ethyl | n-octyl | 68 | 5-Ethyl | propargyl |
| 49 | 6-Ethyl | n-octyl | 69 | 6-Ethyl | propargyl |
| 50 | 5-NO₂ | n-octyl | 70 | 5-NO₂ | propargyl |
| 51 | 6-NO₂ | n-octyl | 71 | 6-NO₂ | propargyl |
| 52 | 5-Cl | allyl | 72 | 5-Cl | benzyl |
| 53 | 6-Cl | allyl | 73 | 6-Cl | benzyl |
| 54 | 5-F | allyl | 74 | 5-F | benzyl |
| 55 | 6-F | allyl | 75 | 6-F | benzyl |
| 56 | 5-OMe | allyl | 76 | 5-OMe | benzyl |
| 57 | 6-OMe | allyl | 77 | 6-OMe | benzyl |
| 58 | 5-Ethyl | allyl | 78 | 5-Ethyl | benzyl |
| 59 | 6-Ethyl | allyl | 79 | 6-Ethyl | benzyl |
| 60 | 5-NO₂ | allyl | 80 | 5-NO₂ | benzyl |

TABLE 2-continued

| | | Examples 42–81 | | | |
|---|---|---|---|---|---|
| Example # | R[1] | R[2] | Example # | R[1] | R[2] |
| 61 | 6-NO$_2$ | allyl | 81 | 6-NO$_2$ | benzyl |

EXAMPLE 82

In Vitro Assay of Antifungal Activity

The in vitro antifungal activity of the compounds of the present invention against a variety of fungi was determined as follow: Test medium was prepared by dissolving first 5 g of dextrose and then 6.7 g of Bacto Yeast Nitrogen Base ® (commercially available from Difco Laboratories) in 100 mL of distilled water. The solution was filter-sterilized and diluted 1:10 with 0.01M pH 8.0 phosphate buffer solution, and the final pH of the medium adjusted to about pH 7.0 when necessary with either 0.1N hydrochloric acid solution of 0.1N sodium hydroxide solution. Next, a stock solution of each compound to be tested was prepared in water or an organic solvent in which the compound was found to be completely soluble at 1 mg/mL. These concentrated stock solutions were diluted to a concentration of 200 µg/mL (twice the highest concentration desired for testing) with the test medium. Amphotericin B, similarly prepared, was used as a reference antifungal agent.

The test organisms were then inoculated into test tubes containing approximately 3 to 10 mL of test medium and the test tubes incubated overnight at 37° C. A sample of each overnight culture was placed in a test tube and diluted using the test medium until a reading of 95% transmittance was obtained in a conventional UV/visible spectrophotometer set to 560 nm. The adjusted cultures were then diluted 1:50 with test medium. These diluted cultures served as the inocula for the assays which follow and were used within 15 minutes of preparation.

Next, 2-fold serial dilutions of each test compound in test medium were prepared in a 96-well microtiter plate using calibrated microdiluters attached to an automatic (hand-held) diluter (available from Dynatech Laboratories). The last well of each row did not receive test compound and served as a growth control.

Using sterile calibrated droppers or a multi-point dispenser, the diluted inoculum suspension was added to each of the wells in the plate. When inoculation was complete, the microtiter tray was covered with a plastic plate sealer to minimize evaporation. After the plate had been sealed, a hole was made above each well with a sterile 26-gauge syringe needle in order to allow gas exchange. If plate sealers were not available, the microtiter trays were stacked in groups of five or less with an empty tray on top. The microtiter trays were then incubated in a humidified chamber at 35°–37° C. for 48 hours or until growth was visible in the growth control wells.

After incubation, each well was observed for the presence or absence of microorganism growth. The minimum inhibitory concentration (MIC) was defined as the lowest concentration of test compound yielding no growth, a slight haze or sparsely isolated colonies on the inoculum spot as compared to the growth control containing no test compound.

The results, which demonstrate the in vitro antifungal activity of the compounds of the present invention, are represented by the data in Tables 3–9, below.

TABLE 3

In Vitro Antifungal Activity of Examples 1–5

| | MIC (µg/mL) | | | | |
|---|---|---|---|---|---|
| ORGANISM | Ex. 1 | Ex. 2 | Ex. 3 | Ex. 4 | Ex. 5 |
| Candida albicans ATCC 10231 | 0.78 | 1.56 | 0.78 | 0.78 | 0.39 |
| Candida albicans 579A | 0.39 | 1.56 | 0.78 | 0.78 | 0.2 |
| Candida albicans CCH 442 | 1.56 | 1.56 | 0.78 | 0.78 | 0.78 |
| Candida albicans ATCC 38247 | 1.56 | | 3.12 | 3.12 | 0.78 |
| Candida albicans ATCC 62376 | 0.78 | 0.78 | 0.78 | 0.78 | 0.78 |
| Candida tropicalis NRRL-Y-112 | 3.12 | 1.56 | 0.78 | 50 | 0.78 |
| Candida kefyr ATCC 28838 | 0.78 | 1.56 | 0.2 | 0.78 | 0.39 |
| Torulopsis glabrata ATCC 15545 | 1.56 | 0.78 | 0.78 | 0.78 | 0.39 |
| Cryptococcus albidus ATCC 34140 | 3.12 | 3.12 | 3.12 | 6.25 | 3.12 |
| Aspergillus niger ATCC 16404 | 3.12 | 3.12 | 6.25 | 0.39 | 0.39 |

TABLE 4

In Vitro Antifungal Activity of Examples 6–12

| | MIC (µg/mL) | | | | |
|---|---|---|---|---|---|
| ORGANISM | Ex. 6 | Ex. 7 | Ex. 8 | Ex. 10 | Ex. 12 |
| Candida albicans ATCC 10231 | 0.2 | 1.56 | 1.56 | 0.39 | 0.39 |
| Candida albicans 579A | 0.2 | 0.78 | 6.25 | 0.39 | 0.78 |
| Candida albicans CCH 442 | 0.2 | 1.56 | 6.25 | 0.78 | 0.78 |
| Candida albicans ATCC 38247 | 0.39 | 1.56 | 6.25 | 6.25 | |
| Candida albicans ATCC 62376 | 0.1 | 1.56 | 6.25 | 0.39 | 0.39 |
| Candida tropicalis NRRL-Y-112 | 0.2 | 1.56 | 3.12 | 0.78 | 1.56 |
| Candida kefyr ATCC 28838 | 0.1 | 0.78 | 1.56 | 0.2 | 0.78 |
| Torulopsis glabrata ATCC 15545 | 0.2 | 1.56 | 3.12 | 0.39 | 0.39 |
| Cryptococcus albidus ATCC 34140 | 3.12 | 6.25 | 12.5 | 3.12 | 1.56 |
| Aspergillus niger ATCC 16404 | 0.2 | 0.78 | 1.56 | 0.2 | 1.56 |

TABLE 5

In Vitro Antifungal Activity of Examples 14–19

| | MIC (µg/mL) | | | | |
|---|---|---|---|---|---|
| ORGANISM | Ex. 14 | Ex. 15 | Ex. 16 | Ex. 18 | Ex. 19 |
| Candida albicans ATCC 10231 | 1.56 | 1.56 | 6.25 | 12.5 | 50 |
| Candida albicans 579A | 1.56 | 3.12 | 3.12 | 12.5 | 50 |
| Candida albicans CCH 442 | 1.56 | 1.56 | 1.56 | 12.5 | 100 |
| Candida albicans ATCC 38247 | 6.25 | 25 | 1.56 | 1.56 | 100 |
| Candida albicans ATCC 62376 | 0.78 | 1.56 | 6.25 | 25 | 100 |
| Candida tropicalis NRRL-Y-112 | 3.12 | 3.12 | 12.5 | 12.5 | 25 |
| Candida kefyr ATCC 28838 | 0.2 | 0.78 | 0.78 | 0.78 | 1.56 |
| Torulopsis glabrata ATCC 15545 | 1.56 | 1.56 | 6.25 | 6.25 | 6.25 |
| Cryptococcus albidus ATCC 34140 | 3.12 | 12.5 | 6.25 | 1.56 | 12.5 |
| Aspergillus niger ATCC 16404 | 0.78 | 1.56 | 3.12 | 6.25 | 12.5 |

TABLE 6

In Vitro Antifungal Activity of Examples 20–24

| | MIC (µg/mL) | | | | |
|---|---|---|---|---|---|
| ORGANISM | Ex. 20 | Ex. 21 | Ex. 22 | Ex. 23 | Ex. 24 |
| Candida albicans ATCC 10231 | 25 | 6.25 | 100 | 50 | 25 |
| Candida albicans 579A | 25 | 6.25 | 100 | 50 | 25 |
| Candida albicans CCH 442 | 50 | 6.25 | 100 | 50 | 25 |
| Candida albicans ATCC 38247 | 3.12 | 6.25 | 50 | 12.5 | 12.5 |
| Candida albicans ATCC 62376 | 25 | 6.25 | 100 | 50 | 25 |
| Candida tropicalis NRRL-Y-112 | 25 | 6.25 | 100 | 50 | 25 |
| Candida kefyr ATCC 28838 | 1.56 | 0.78 | 3.12 | 3.12 | 0.78 |
| Torulopsis glabrata ATCC 15545 | 25 | 3.12 | 100 | 50 | 12.5 |
| Cryptococcus albidus ATCC 34140 | 12.5 | 12.5 | 100 | 12.5 | 12.5 |
| Aspergillus niger ATCC 16404 | 12.5 | 1.56 | 25 | 12.5 | 3.12 |

TABLE 7

In Vitro Antifungal Activity of Examples 25-29

| | MIC (μg/mL) | | | | |
|---|---|---|---|---|---|
| ORGANISM | Ex. 25 | Ex. 26 | Ex. 27 | Ex. 28 | Ex. 29 |
| *Candida albicans* ATCC 10231 | 6.25 | 1.56 | 1.56 | 3.12 | 6.25 |
| *Candida albicans* 579A | 3.12 | 3.12 | 0.78 | 3.12 | 12.5 |
| *Candida albicans* CCH 442 | 1.56 | 3.12 | 1.56 | 3.12 | 25 |
| *Candida albicans* ATCC 38247 | 1.56 | 12.5 | 3.12 | 6.25 | 50 |
| *Candida albicans* ATCC 62376 | 6.25 | 1.56 | 0.78 | 3.12 | 6.25 |
| *Candida tropicalis* NRRL-Y-112 | 12.5 | 3.12 | 1.56 | 3.12 | 12.5 |
| *Candida kefyr* ATCC 28838 | 3.12 | 0.78 | 0.39 | 0.39 | 3.12 |
| *Torulopsis glabrata* ATCC 15545 | 6.25 | 3.12 | 0.78 | 3.12 | 12.5 |
| *Cryptococcus albidus* ATCC 34140 | 12.5 | 6.25 | 3.12 | 12.5 | 25 |
| *Aspergillus niger* ATCC 16404 | 3.12 | 0.78 | 0.39 | 0.78 | 3.12 |

TABLE 8

In Vitro Antifungal Activity of Examples 30-36

| | MIC (μg/mL) | | | | |
|---|---|---|---|---|---|
| ORGANISM | Ex. 30 | Ex. 31 | Ex. 34 | Ex. 35 | Ex. 36 |
| *Candida albicans* ATCC 10231 | 25 | 12.5 | 1.56 | 0.78 | 3.12 |
| *Candida albicans* 579A | 12.5 | 25 | 0.78 | 0.78 | 1.56 |
| *Candida albicans* CCH 442 | 25 | 25 | 0.78 | 0.78 | 6.25 |
| *Candida albicans* ATCC 38247 | 25 | 25 | 1.56 | 6.25 | 12.5 |
| *Candida albicans* ATCC 62376 | 25 | 25 | 0.78 | 0.78 | 3.12 |
| *Candida tropicalis* NRRL-Y-112 | 25 | 50 | 50 | 1.56 | 3.12 |
| *Candida kefyr* ATCC 28838 | 12.5 | 12.5 | 0.78 | 0.39 | 0.78 |
| *Torulopsis glabrata* ATCC 15545 | 25 | 12.5 | 50 | 1.56 | 3.12 |
| *Cryptococcus albidus* ATCC 34140 | 25 | 50 | 6.25 | 6.25 | 25 |
| *Aspergillus niger* ATCC 16404 | 12.5 | 12.5 | 0.39 | 0.39 | 3.12 |

TABLE 9

In Vitro Antifungal Activity of Examples 37-41 and Standard

| | MIC (μg/mL) | | | | |
|---|---|---|---|---|---|
| ORGANISM | Ex. 37 | Ex. 39 | Ex. 40 | Ex. 41 | *Std. |
| *Candida albicans* ATCC 10231 | 1.56 | 1.56 | 1.56 | 1.56 | 1.56 |
| *Candida albicans* 579A | 3.12 | 3.12 | 0.78 | 0.78 | 1.56 |
| *Candida albicans* CCH 442 | 6.25 | 3.12 | 3.12 | 3.12 | 1.56 |
| *Candida albicans* ATCC 38247 | 3.12 | 12.5 | 0.2 | 0.39 | 12.5 |
| *Candida albicans* ATCC 62376 | 6.25 | 3.12 | 1.56 | 1.56 | 1.56 |
| *Candida tropicalis* NRRL-Y-112 | 6.25 | 6.25 | 3.12 | 3.12 | 1.56 |
| *Candida kefyr* ATCC 28838 | 1.56 | 1.56 | 0.78 | 0.78 | 1.56 |
| *Torulopsis glabrata* ATCC 15545 | 6.25 | 3.12 | 3.12 | 3.12 | 3.12 |
| *Cryptococcus albidus* ATCC 34140 | 12.5 | 25 | 3.12 | 6.25 | 3.12 |
| *Aspergillus niger* ATCC 16404 | 3.12 | 1.56 | 1.56 | 1.56 | 3.12 |

*Std. = Standard = Amphotericin B

The foregoing Examples are merely illustrative of the present invention and are not intended to limit the invention to the disclosed compounds. It is understood that variations and changes which are obvious to one skilled in the art will be regarded as being within the scope and spirit of the invention, which are defined exclusively by the appended claims and their equivalents.

What is claimed is:

1. A compound having the formula

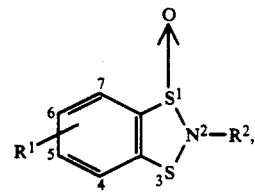

wherein
$R^1$ is a substituent on the 4-, 5-, 6- or 7-position of the benzodithiazole nucleus selected from the group consisting of
  (1) hydrogen,
  (2) $(C_1-C_4)$alkyl,
  (3) halogen,
  (4) halo-$(C_1-C_4)$alkyl,
  (5) $(C_1-C_4)$alkoxy, and
  (6) nitro; and
$R^2$ is selected from the group consisting of
  (1) $(C_1-C_{12})$alkyl;
  (2) $(C_1-C_{12})$alkyl substituted with a substituent selected from the group consisting of
    (i) hydroxy,
    (ii) $-OS(O)^2R^3$ wherein $R^3$ is $(C_1-C_4)$alkyl,
    (iii) $-OSiR^4R^5R^6$ wherein $R^4$, $R^5$ and $R^6$ are independently selected from the group consisting of methyl, ethyl, t-butyl and phenyl,
    (iv) $-CHO$ or $-C(OR^7)_2$ wherein $R^7$ is methyl or ethyl,
    (v) $-OC(O)R^8$ wherein $R^8$ is $(C_1-C_4)$alkyl, and
    (vi) $-C(O)OR^{10}$ wherein $R^{10}$ is $(C_1-C_4)$alkyl;
  (3) $(C_2-C_{16})$alkenyl;
  (4) $(C_2-C_{16})$alkynyl;
  (5) $(C_3-C_{10})$cycloalkyl;
  (6) $(C_6-C_{10})$aryl;
  (7) $(C_6-C_{10})$aryl substituted with 1 or 2 substituents selected from the group consisting of
    (i) halogen,
    (ii) halo-$(C_1-C_4)$alkyl,
    (iii) $(C_1-C_4)$alkoxy,
    (iv) $-CHO$ or $-C(OR^7)_2$ wherein $R^7$ is methyl or ethyl,
    (v) $-C(O)OR^{10}$ wherein $R^{10}$ is $(C_1-C_4)$alkyl, and
    (vi) $-NR^{11}R^{12}$ wherein $R^{11}$ and $R^{12}$ are $(C_1-C_4)$alkyl;
  (8) $(C_6-C_{10})$aryl-$(C_1-C_4)$alkyl; and
  (9) $(C_6-C_{10})$aryl-$(C_1-C_4)$alkyl wherein the aryl group is substituted with 1 or 2 substituents selected from the group consisting of
    (i) halogen,
    (ii) $(C_1-C_4)$alkyl,
    (iii) halo-$(C_1-C_4)$alkyl,
    (iv) $(C_1-C_4)$alkoxy, and
    (v) $-NR^{11}R^{12}$ wherein $R^{11}$ and $R^{12}$ are $(C_1-C_4)$alkyl;
or a pharmaceutically acceptable salt thereof.

2. A compound according to claim 1 wherein which $R^2$ is selected from $(C_1-C_9)$alkyl, $(C_3-C_9)$alkenyl, $(C_3-C_9)$alkynyl and phenyl-$(C_1-C_4)$alkyl.

3. A compound according to claim 1 selected from the group consisting of 2-(2-phenylethyl)-1,3,2-benzodithiazole-1-oxide;
2-methyl-1,3,2-benzodithiazole-1-oxide;
2-n-propyl-1,3,2-benzodithiazole-1-oxide;
2-n-pentyl-1,3,2-benzodithiazole-1-oxide;

2-n-heptyl-1,3,2-benzodithiazole-1-oxide;
2-n-octyl-1,3,2-benzodithiazole-1-oxide;
2-n-nonyl-1,3,2-benzodithiazole-1-oxide;
2-n-decyl-1,3,2-benzodithiazole-1-oxide;
2-n-hexadecyl-1,3,2-benzodithiazole-1-oxide;
2-allyl-1,3,2-benzodithiazole-1-oxide;
2-oleyl-1,3,2-benzodithiazole-1-oxide;
2-propargyl-1,3,2-benzodithiazole-1-oxide;
2-(3-pentyl)-1,3,2-benzodithiazole-1-oxide;
2-t-butyl-1,3,2-benzodithiazole-1-oxide;
2-(3,3-dimethylpropyl)-1,3,2-benzodithiazole-1-oxide;
2-(1,1,3,3-tetramethylbutyl)-1,3,2-benzodithiazole-1-oxide;
2-(2-methoxy-1-methylethyl)-n-nonyl-1,3,2-benzodithiazole-1-oxide;
2-(2-hydroxyethyl)-1,3,2-benzodithiazole-1-oxide;
O-(2-(1,3,2-benzodithiazole-2-yl-1-oxide)ethyl)methanesulfonate;
2-(2-(triethylsilyloxy)ethyl)-1,3,2-benzodithiazole-1-oxide;
ethyl 2-(1,3,2-benzodithiazole-2-yl-1-oxide)-acetate;
2-(2-(1,3,2-benzodithiazole-2-yl-1-oxide)ethyloxy) acetic acid;
2(3-(N,N-dimethylamino)-n-propyl)-1,3,2-benzodithiazole-1-oxide;
2-(4,4-diethoxybutyl)-1,3,2-benzodithiazole-1-oxide;
methyl 8-(1,3,2-benzodithiazole-2-yl)-octanoate;
2-cyclopropyl-1,3,2-benzodithiazole-1-oxide;
2-cyclooctyl-1,3,2-benzodithiazole-1-oxide;
2-(2-adamantyl)-1,3,2-benzodithiazole-1-oxide;
2-phenyl-1,3,2-benzodithiazole-1-oxide;
2-(3,4-difluorophenyl)-1,3,2-benzodithiazole-1-oxide;
2-benzyl-1,3,2-benzodithiazole-1-oxide;
2-(2,4-dichlorophenyl)methyl-1,3,2-benzodithiazole-1-oxide;
2-(4-(dimethylamino)phenyl)methyl-1,3,2-benzodithiazole-1-oxide
2-(3-phenylpropyl)-1,3,2-benzodithiazole-1-oxide;
2-n-octyl-5-methyl-1,3,2-benzodithiazole-1-oxide;
2-n-octyl-6-methyl-1,3,2-benzodithiazole-1-oxide;
2-phenylmethyl-5-methyl-1,3,2-benzodithiazole-1-oxide;
2-phenylmethyl-6-methyl-1,3,2-benzodithiazole-1-oxide;
5-chloro-2-n-octyl-1,3,2-benzodithiazole-1-oxide;
6-chloro-2-n-octyl-1,3,2-benzodithiazole-1-oxide;
5-fluoro-2-n-octyl-1,3,2-benzodithiazole-1-oxide;
6-fluoro-2-n-octyl-1,3,2-benzodithiazole-1-oxide;
5-methoxy-2-n-octyl-1,3,2-benzodithiazole-1-oxide;
6-methoxy-2-n-octyl-1,3,2-benzodithiazole-1-oxide;
5-ethyl-2-n-octyl-1,3,2-benzodithiazole-1-oxide;
6-ethyl-2-n-octyl-1,3,2-benzodithiazole-1-oxide;
5-nitro-2-n-octyl-1,3,2-benzodithiazole-1-oxide;
6-nitro-2-n-octyl-1,3,2-benzodithiazole-1-oxide;
2-allyl-5-chloro-1,3,2-benzodithiazole-1-oxide;
2-allyl-6-chloro-1,3,2-benzodithiazole-1-oxide;
2-allyl-5-fluoro-1,3,2-benzodithiazole-1-oxide;
2-allyl-6-fluoro-1,3,2-benzodithiazole-1-oxide;
2-allyl-5-methoxy-1,3,2-benzodithiazole-1-oxide;
2-allyl-6-methoxy-1,3,2-benzodithiazole-1-oxide;
2-allyl-5-ethyl-1,3,2-benzodithiazole-1-oxide;
2-allyl-6-ethyl-1,3,2-benzodithiazole-1-oxide;
2-allyl-5-nitro-1,3,2-benzodithiazole-1-oxide;
2-allyl-6-nitro-1,3,2-benzodithiazole-1-oxide;
5-chloro-2-propargyl-1,3,2-benzodithiazole-1-oxide;
6-chloro-2-propargyl-1,3,2-benzodithiazole-1-oxide;
5-fluoro-2-propargyl-1,3,2-benzodithiazole-1-oxide;
6-fluoro-propargyl-1,3,2-benzodithiazole-1-oxide;
5-methoxy-propargyl-1,3,2-benzodithiazole-1-oxide;
6-methoxy-propargyl-1,3,2-benzodithiazole-1-oxide;
5-ethyl-2-propargyl-1,3,2-benzodithiazole-1-oxide;
6-ethyl-2-propargyl-1,3,2-benzodithiazole-1-oxide;
5-nitro-2-propargyl-1,3,2-benzodithiazole-1-oxide;
6-nitro-2-propargyl-1,3,2-benzodithiazole-1-oxide;
2-benzyl-5-chloro-1,3,2-benzodithiazole-1-oxide;
2-benzyl-6-chloro-1,3,2-benzodithiazole-1-oxide;
2-benzyl-5-fluoro-1,3,2-benzodithiazole-1-oxide;
2-benzyl-6-fluoro-1,3,2-benzodithiazole-1-oxide;
2-benzyl-5-methoxy-1,3,2-benzodithiazole-1-oxide;
2-benzyl-6-methoxy-1,3,2-benzodithiazole-1-oxide;
2-benzyl-5-ethyl-1,3,2-benzodithiazole-1-oxide;
2-benzyl-6-ethyl-1,3,2-benzodithiazole-1-oxide;
2-benzyl-5-nitro-1,3,2-benzodithiazole-1-oxide; and
2-benzyl-6-nitro-1,3,2-benzodithiazole-1-oxide;
and pharmaceutically acceptable salts thereof.

4. A compound according to claim 3 selected from the group consisting of 2-n-heptyl-1,3,2-benzodithiazole-1-oxide;
2-n-octyl-1,3,2-benzodithiazole-1-oxide;
2-allyl-1,3,2-benzodithiazole-1-oxide;
2-propargyl-1,3,2-benzodithiazole-1-oxide; and
2-phenylmethyl-1,3,2-benzodithiazole-1-oxide;
and pharmaceutically acceptable salts thereof.

5. A pharmaceutical composition comprising a therapeutically effective amount of a compound according to claim 1 and a pharmaceutically acceptable carrier.

6. A pharmaceutical composition comprising a therapeutically effective amount of a compound according to claim 3 and a pharmaceutically acceptable carrier.

7. A composition according to claim 6 wherein the compound is selected from the group consisting of 2-n-heptyl-1,3,2-benzodithiazole-1-oxide;
2-n-octyl-1,3,2-benzodithiazole-1-oxide;
2-allyl-1,3,2-benzodithiazole-1-oxide;
2-propargyl-1,3,2-benzodithiazole-1-oxide; and
2-phenylmethyl-1,3,2-benzodithiazole-1-oxide;
and pharmaceutically acceptable salts thereof.

8. A method for treating fungal infections in humans and other mammals which comprises administering a therapeutically effective amount of a compound according to claim 1.

9. A method according to claim 8 wherein the compound is selected from the group consisting of 2-n-heptyl-1,3,2-benzodithiazole-1-oxide;
2-n-octyl-1,3,2-benzodithiazole-1-oxide;
2-allyl-1,3,2-benzodithiazole-1-oxide;
2-propargyl-1,3,2-benzodithiazole-1-oxide; and
2-phenylmethyl-1,3,2-benzodithiazole-1-oxide;
and pharmaceutically acceptable salts thereof.

* * * * *